US006337836B1

(12) United States Patent
Eidelson

(10) Patent No.: US 6,337,836 B1
(45) Date of Patent: Jan. 8, 2002

(54) PROGRAMMABLE ELECTRONIC LABEL

(76) Inventor: Arthur F. Eidelson, 4904 Bunclody Ct., Richmond, VA (US) 23228

( * ) Notice: Subject to any disclaimer, the term of this patent is extended or adjusted under 35 U.S.C. 154(b) by 0 days.

(21) Appl. No.: 09/323,460

(22) Filed: Jun. 1, 1999

(51) Int. Cl.[7] .......................... G04B 47/00; G04B 37/00; G07F 11/00; G07F 17/60
(52) U.S. Cl. .................. 368/10; 368/276; 368/280; 221/2; 235/375; 705/2; 705/28
(58) Field of Search ............................ 368/10, 82–84, 368/223, 239–242, 72–74, 250, 251; 235/375–377, 380, 385; 221/2, 3, 15; 705/2, 3, 15, 28, 418

(56) References Cited

U.S. PATENT DOCUMENTS

| | | | |
|---|---|---|---|
| 4,730,285 A | * 3/1988 | Lie | 368/90 |
| 4,875,174 A | 10/1989 | Olodort et al. | 364/519 |
| 4,918,631 A | * 4/1990 | Hara et al. | 364/708 |
| 5,313,439 A | 5/1994 | Albeck | 368/10 |
| 5,327,115 A | 7/1994 | Swierczek | 340/309.15 |
| 5,418,760 A | * 5/1995 | Kawashima et al. | 368/69 |
| 5,555,223 A | 9/1996 | Barainsky | 368/10 |
| 5,625,334 A | 4/1997 | Compton | 340/309.15 |
| 5,640,306 A | 6/1997 | Gaumet et al. | 361/737 |
| 5,751,257 A | 5/1998 | Sutherland | |
| 5,802,015 A | 9/1998 | Rothschild | 368/10 |
| 5,884,271 A | * 3/1999 | Pitrona | 705/1 |
| 5,889,737 A | 3/1999 | Alameh et al. | |
| 5,931,764 A | 8/1999 | Freeman et al. | 482/4 |

FOREIGN PATENT DOCUMENTS

| | | |
|---|---|---|
| DE | 90 04 197 | 6/1990 |
| DE | 91 11 380 | 1/1992 |
| DE | 198 25 533 A1 | 12/1999 |
| EP | 0 785 527 A2 | 1/1997 |
| FR | 2 650 095 | 6/1990 |
| WO | WO 99/07189 | 2/1999 |

OTHER PUBLICATIONS

UbiQ,Inc., "Answers to Frequently Asked Questions About Smart Cards", Internet article viewable at www.ubiqinc-.com/ansrpage1.cfm.
Dallas Semiconductor Corp, Dallas Semiconductor Wraps ICs in Durable Film to Create Smallest Chip–Scale Package (CSP), News Release, Dec. 18, 1998, Internet article viewable at www.dalsemi.com/News_Center/Press_Releases/1998/pr_csp.html.
Frautschi, Mark A. Ph.D., "Embedded Systems and the Year 2000 Problem (The OTHER Year 2000 Problem)", Apr. 6, 1999, Internet article viewable at www.tmn.com/~frautsch/y2k2.html.
Gemplus Corporation, "Gem Wave Industrial Smart Labels", Products Specifications, Dec. 1998.
Gemplus, "Gem Wave Smart Labels", Product Sheet, Internet article dated no later than Apr. 16, 1999 viewable at pluton.gemplus.fr.
Philips Semiconductors, "Business News from Phillips Semiconductors", Jan. 1999, Internet article viewable at www–us.semiconductors.philips.com.
Philips Semiconductors, "Low Power Clock/Calendar", Product Specification, Mar. 25, 1997.

(List continued on next page.)

Primary Examiner—Vit Miska
(74) Attorney, Agent, or Firm—McGuireWoods LLP

(57) ABSTRACT

A programmable electronic reminder device for providing a signal at a selectively predetermined date and time includes a programmable real time clock circuit, a thin, sheet-like battery, a light emitting polymer for illuminating a predetermined alert message and a programming interface mounted to a pliant substrate in a layered arrangement. The reminder device is configured as a card or label on which human readable indicia corresponding to the predetermined date and time may be printed.

29 Claims, 4 Drawing Sheets

OTHER PUBLICATIONS

Cambridge Display Technology, Ltd., "Cambridge Display Technology Announces Investment by Intel Corporation", Nov. 10, 1997, Internet article viewable at www.cdtltd.co.uk.

Cambridge Display Technology, Ltd., "DuPont and CDT Target Flexible Displays", Mar. 26, 1998, Internet article viewable at www.cdtltd.co.uk.

Cambridge Display Technology, Ltd., "CDT and Seiko–Epson Demonstrate World's First Plastic Television Screen", Feb. 16, 1998, Internet article viewable at www.cdtltd.co.uk.

Microsoft Daily News, "Glowing Plastic Monitors", Feb. 16, 1998, Internet article viewable at www.zdnet.com.

Philips Research, Press Release, Mar. 1998, Internet article viewable at www.research.philips.com.

Electro Chemical Research, "Batteries:Background", Internet article viewable at www.ecr.co.il.

All Flex, Inc., Internet article viewable at Home Page www.allflex.thomasregister.com.

Texas Instruments, "Texas Instruments Introduces Tag–It––The First Smart Label Technology Designed to Counteract the Threat of Counterfeit Products", Jan. 23, 1998, Internet article viewable at www.ti.com.

Zebra Technologies —Press Release, Oct. 8, 1998, Internet article viewable at www.zebra.com.

Dallas Semiconductor Corp. Tech. Brief 8, "Problems and Solutions for the Year 2000", Oct. 19, 1998, Internet article viewable at www.dalsemi.com.

Texas Instruments, "Tag–it–The New World of Electronic Smart Labels Arrives at Scan–Tech '98", Press Release, Sep. 14, 1998.

Battery Engineering, "What'New", Internet article viewable at www.batteryeng.com.

Dallas Semiconductor, Product Specification for Memory iButtons, Feb. 6, 1998.

* cited by examiner

PROGRAMMABLE ELECTRONIC LABEL

BACKGROUND OF THE INVENTION

The present invention relates broadly to time-based alarm devices. More specifically, the present invention relates to cards, labels and other indicia carrying devices that provide perceptible signals at a predetermined date and time.

In many industries tracking time intervals is an important function of manufacturing, or other areas where the shelf life of materials may be a concern. Often, critical dates and times are tracked on a periodic basis by individuals over long time intervals. In industries like the pharmaceutical industry, the employees may be charged with monitoring the due dates for recalibration of critical instruments or machinery. This is also true in service providing industries. For example, doctors or dentists often want their patients to make a return visit after a specific interval has passed. The patient is charged with keeping track of the appointment date.

The tracking of critical dates and times is typically accomplished through periodic, manual comparison of the critical date to the current date. This is often assisted by affixing or printing of the critical date in a location that facilitates visual inspection. Food and drug products, for example, have expiration dates printed on their containers that should be examined before use to determine if their expiration dates have passed. In another area, information regarding an appointment is typically provided to a patient in the form of a business card with a handwritten date and time printed on its face. The patient must post this information in a way that will allow him to remember the appointment after months have passed. In the pharmaceutical industry, it is common practice to attach stickers to instruments requiring periodic recalibration. These stickers typically show the date of the last calibration along with the due date of the next calibration. Such instruments may number in the thousands and must be constantly tracked through manual or computerized reminder systems.

These methods all place reliance on individuals to regularly check the date and mentally compare it to the current date. If these individuals are insufficiently diligent, the critical date may be missed. Recalibration dates, in particular, are likely to be missed because of the number of instruments involved. The potential consequences of the use of instruments that are out of calibration include high scrap rates, product recalls and even product liability claims.

It is therefore desirable to provide a simple device that provides a perceptible alert on the arrival or approach of a critical date, time or both, that is configured as a replacement for cards and labels. Previous attempts to provide signaling devices for attachment to equipment or perishable goods have resulted in relatively bulky devices that potentially interfere with the use of the instrument or product to which they are attached. In addition, these devices have been inaccurate or unable to function over a long periods of time and have been too costly to provide a viable alternative to regular human inspection.

There is accordingly a need for an improved device for tracking critical dates. In one form, the device would provide an improved way for businesses to provide customers with reminders to return goods or to come in for appointments. In another form, the device would alert users of time-critical goods or hardware that an expiration date or other critical date has been reached. Ideally, the improvement could be easily and cheaply incorporated without significant change to product packaging or inspection/recalibration procedures.

SUMMARY OF THE INVENTION

It is therefore an object of the present invention to provide an electronic reminder device that provides a perceptible signal when a predetermined absolute date and time are reached.

It is another object of the present invention to provide such a reminder device that is card-like in size and appearance for use as a specialized business or appointment card.

It is yet another object of the present invention that the predetermined date and time be easily programmed into the electronic reminder device using a user-friendly programming device.

It is also an object of the present invention to provide an electronic reminder device that is formed from thin, flexible components.

It is a further object of the present invention that the electronic reminder device include human readable text or graphics printed thereon to facilitate the use of the reminder device as a visual reference.

It is also an object of the present invention to provide an electronic label having a low power consumption to permit the label to operate over relatively long intervals.

It is a further object of the present invention to incorporate a highly accurate real time clock into the electronic reminder device so that the critical date and time may be programmed into the label as an absolute date and time rather than as an interval.

Another object of the present invention is to provide a thin, flexible electronic label that provides a perceptible signal when a predetermined absolute date and time are reached. Such an electronic label would have the attributes of the electronic reminder device of the present invention and additionally may be easily attached to a variety of surface textures and geometries.

It is another object of the present invention to provide a system for providing electronic labels for signaling that a predetermined date and time has been reached where the system includes a supply of programmable electronic labels, a programming device such as a computer, and a label printer.

To those ends, a programmable electronic indicia carrying device for providing a signal at a selective predetermined date and time includes a pliant substrate to which a real time clock circuit is attached. The real time clock circuit is selectively programmable to provide an alarm signal substantially coincident with the predetermined date and time. The indicia carrying device further includes an enunciator operatively connected to the real time clock circuit. This enunciator provides a perceptible indication in response to the alarm signal. The indicia carrying device also includes a programming interface operatively connected to the real time clock circuit whereby the predetermined date and time may be programmed into the real time clock circuit.

The real time clock circuit of a programmable electronic indicia carrying device according to the present invention preferably includes a sheet-like, generally pliant battery operatively connected to the real time clock circuit. The enunciator preferably includes a visual indicator formed from a generally pliant light emitting polymer sheet. The light emitting polymer sheet is configured to provide a visually perceptible indication in response to the alarm signal to indicate that the predetermined date and time has occurred. The visual indicator preferably includes a predetermined message that is revealed in response to the alarm signal. The enunciator may include an audio generator that provides an audible alarm in response to the alarm signal.

The real time clock circuit of a programmable electronic indicia carrying device according to the present invention preferably includes an integrated circuit microprocessor. The real time clock circuit and the enunciator are preferably fixed to the substrate in a layered arrangement.

The programming interface of a programmable electronic indicia carrying device according to the present invention is preferably selectively connectable to a computer for input of date and time data to program the real time clock circuit to emit the alarm signal at the predetermined date and time.

A programmable electronic label for providing a signal at a selectively predetermined expiration date and time includes a pliant label substrate to which is attached a real time clock circuit. The real time clock circuit is selectively programmable to provide an alarm signal substantially coincident with the predetermined expiration date and time. The electronic label further includes an enunciator operatively connected to the real time clock circuit. This enunciator provides a perceptible indication in response to the alarm signal. The electronic label includes a programming interface operatively connected to the real time clock circuit whereby the predetermined date and time may be programmed into the real time clock circuit. The electronic label also includes an arrangement for attaching the programmable electronic label to a surface.

The real time clock circuit of a programmable electronic label according to the present invention preferably includes a sheet-like, generally pliant battery operatively connected to the real time clock circuit. The enunciator preferably includes a visual indicator formed from a generally pliant light emitting polymer sheet. This light emitting polymer sheet is configured to provide a visually perceptible indication in response to the alarm signal to indicate that the predetermined expiration date and time has occurred. The visual indicator preferably includes a predetermined message that is selectively revealed in response to the alarm signal. The enunciator may include an audio generator that provides an audible alarm in response to the alarm signal. The real time clock circuit of the electronic label preferably includes an integrated circuit microprocessor.

A programmable electronic label according to the present invention preferably includes a surface for carrying visually perceptible indicia. The programming interface of an electronic label according to the present invention is selectively connectable to a computer for input of expiration date and time data to program the real time clock circuit to emit the alarm signal at the predetermined expiration date and time.

An electronic labeling system for providing electronic, selectively individually preprogrammed labels that each provide a signal at a selectively predetermined expiration date and time includes a plurality of programmable electronic labels. Each label includes a pliant label substrate to which is attached a real time clock circuit. The real time clock circuit is selectively programmable to provide an alarm signal substantially coincident with the predetermined expiration date and time. Each label also includes an enunciator operatively connected to the real time clock circuit. This enunciator provides a perceptible indication in response to the alarm signal. Also included in each label is a programming interface operatively connected to the real time clock circuit whereby the predetermined expiration date and time may be programmed into the real time clock circuit. Each label further includes an arrangement for attaching the electronic label to a surface. Each programmable electronic label also includes a surface for carrying visually perceptible indicia. The electronic labeling system further includes a communication interface connectable to the programming interface of each electronic programmable label.

The electronic labeling system preferably further includes an arrangement for programming the real time clock circuit to emit the alarm signal at the predetermined time and date. The real time clock circuit preferably includes an integrated circuit microprocessor and a sheet-like, generally pliant battery operatively connected to the real time clock circuit. The enunciator preferably includes a visual indicator formed from a generally pliant light emitting polymer sheet. The light emitting polymer sheet is configured to provide a visually perceptible indication in response to the alarm signal to indicate that the predetermined expiration date and time has occurred. The visual indicator preferably includes a predetermined message that is selectively revealed in response to the alarm signal. The enunciator may include an audio generator that provides an audible alarm in response to the alarm signal.

The electronic labeling system according to the present invention preferably further includes a printer for printing visually perceptible indicia on each programmable electronic label. The printer is preferably operatively interconnected with the communication interface and the arrangement for programming so that the visually perceptible indicia may be printed on each programmable electronic label substantially simultaneously with the programming of each programmable electronic label by the arrangement for programming. The arrangement for programming preferably includes a personal computer. The plurality of electronic programmable labels are preferably removably attached to an elongate backing sheet. The printer is preferably capable of accepting a continuous feed of this backing sheet for individual printing of each electronic programmable label.

The above embodiments achieve the objective of providing a small, programmable indicia carrying reminder device in the form of a card or label.

DESCRIPTION OF THE PREFERRED EMBODIMENT

Figure 1:
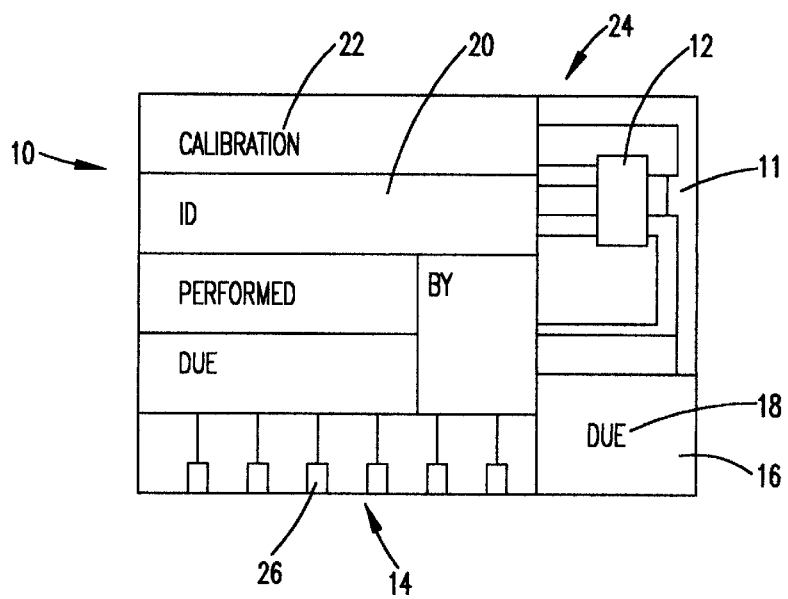
FIG. 1 is a perspective view of a programmable electronic indicia carrying device according to the preferred embodiment of the present invention.

Turning now to the drawings and more particularly to FIG. 1, a programmable electronic indicia carrying reminder device according to the present invention is illustrated generally at 10. The reminder device 10 is generally configured in the nature of a card or label that provides a reminder or warning that a particular date and time of interest—hereinafter referred to as the critical date or expiration date—is approaching or has been reached. When the critical date is reached, the reminder device 10 provides a perceptible alert.

The electronic reminder device 10 includes a programmable real time clock circuit illustrated schematically at 12, a programming interface 14, an illuminable visual indicator 16 having a predetermined alert message 18, and a printing surface 20 upon which informative indicia 22 may be printed. The date and time of interest are programmed into the real time clock circuit 12 through the programming interface 14. When the date and time are reached, the real time clock circuit 12 causes alert indicator 16 to illuminate the predetermined alert message 18.

Figure 2:
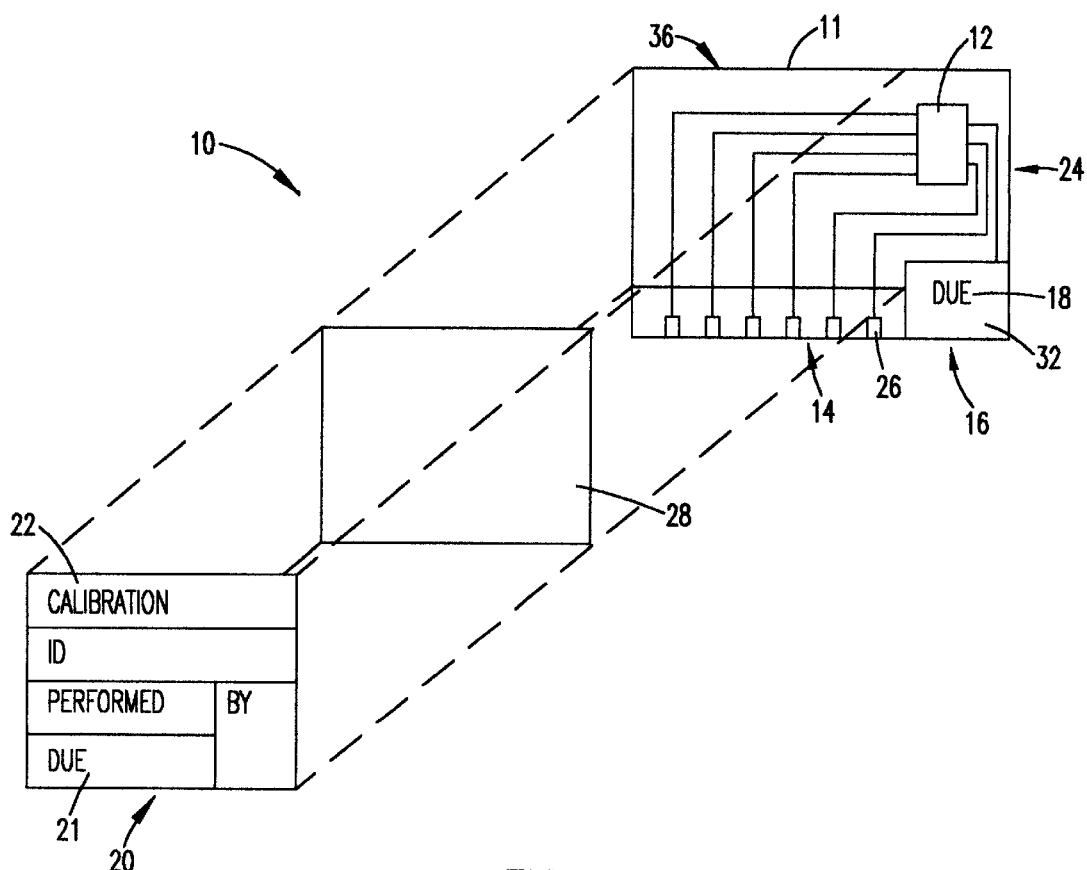
FIG. 2 is an exploded perspective view of a programmable electronic indicia carrying device according to the preferred embodiment of the present invention.

As shown in FIG. 2, the reminder device 10 is designed as a thin, flexible laminate and is formed using Republic Technologies' flexible process. To this end, flexible, low profile components are mounted to a generally pliant polymer substrate 11. These components include the real time clock circuit 12, the programming interface 14, an arrangement of electrical connection traces 24 and the alert indicator 16. An ultrathin sheet-like battery 28 and a printing surface 20 are bonded to a portion of the substrate 11 leaving the programming interface 14 and the alert indicator exposed.

The real time clock circuit 12 includes a crystal controlled integrated circuit real time clock 13 that maintains the absolute date and time. The real time clock 13 is programmable to provide an alarm signal when a particular absolute date and time are reached. The real time clock 13 is a conventionally mounted and packaged chip that is surface mounted to the substrate 11. One commercially available example of a real time clock of this type is Epson's RTC 8593, which provides the accuracy required by the invention with a current draw of only one microampere. The 14-pin RTC 8593 has a thickness of approximately 3.5 mm. Alternatively, the real time clock 13 may be configured as a chip scale package (CSP) mounted to the substrate 11 using solder bumps. A CSP packaged in a durable film, such as those available from Dallas Semiconductor, may be less than 1 mm thick.

In one embodiment of the present invention, the real time clock circuit 12 includes a single-chip microprocessor that includes a real time clock as a feature. The microprocessor contains an operating system based on the Java programming language, thereby allowing high-end Java applets to support a variety of data processing applications. This would permit, in addition to the storage of expiration date and time information, storage of calibration data, patient historical data, or other vital information that can be retrieved and processed by a personal computer.

The programming interface 14 includes electrical conductor pads 26 affixed to one surface of the substrate. These electrical conductor pads 26 are electrically connected to the real time clock circuit 12 by the arrangement of electrical connection traces 24 printed on the substrate 11. The electrical conductor pads 26 are arranged so that the programming interface 14 may be operatively connected to a programming arrangement through a flex programming connector 30 such as that illustrated in FIG. 3. Alternatively, other programming interface arrangements may be used. For example, the programming interface 14 could include an Infrared Data Association compliant infrared data link or an electromagnetic data link having a laminated metal antenna.

The alert indicator or annunciator 16 is formed as a light emitting polymer sheet 32. Light emitting polymers are plastics developed by Cambridge Display Technology that are electroluminescent; that is, plastics that produce light when subjected to an electric potential. In the present invention, illumination of the light emitting polymer sheet 32 is triggered by the alarm signal produced by the real time clock 13. The thin light-emitting polymer sheet measures approximately 0.25 inches by 0.50 inches and requires current consumption of less than one milliampere for illumination.

Figures 3, 4:
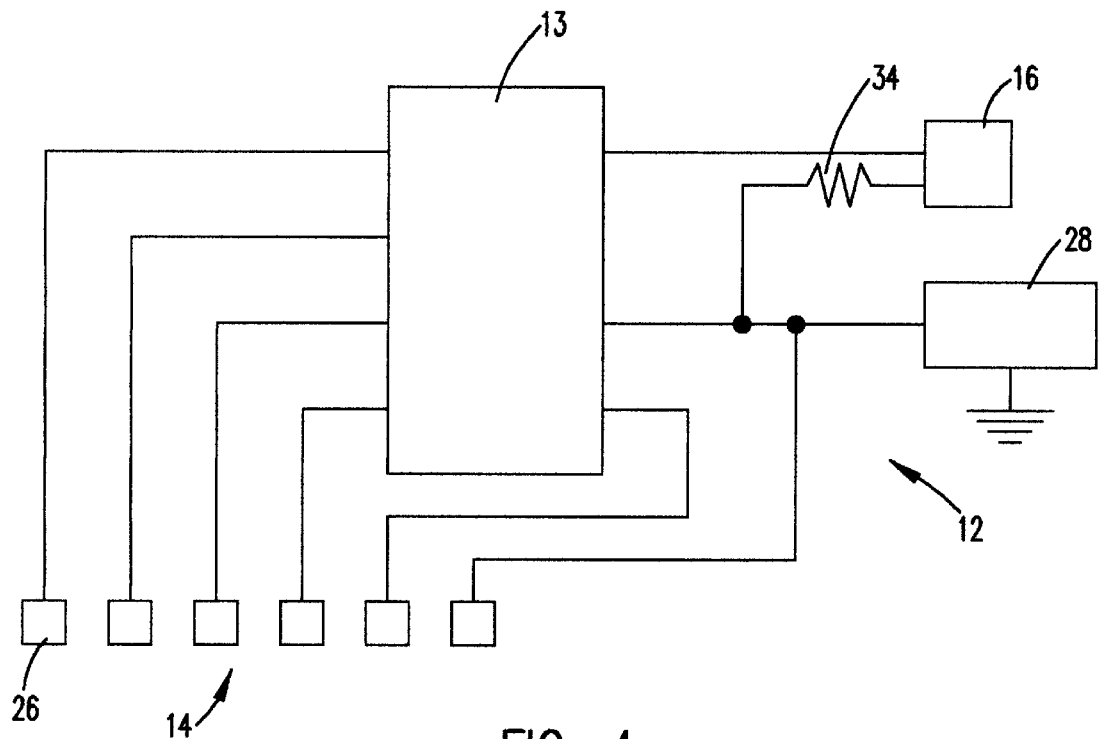
FIG. 3 is a perspective view of a 1 mm flexible programming connector.
FIG. 4 is a schematic representation of the electrical circuit of the electronic label according to the preferred embodiment of the present invention.

As illustrated schematically in FIG. 4, the light emitting polymer sheet 32 is electrically connected to the real time clock 13 and a battery 28. The low current consumption of the light emitting polymer sheet 32 allows for direct drive by the real time clock 13 with an approximately three k-ohm resistor 34 providing current limiting. The real time clock 13 may be programmed to cause the light emitting polymer sheet 32 to be intermittently illuminated. This has the dual advantage of making the signal more conspicuous and enhancing battery life. It will be understood by those skilled in the art that other components such as panels woven from light emitting plastic fibers may also be used as an illumination source for the alert indicator. Other components, such as light-emitting diodes, are usable but have size and current draw disadvantages not presented by the light-emitting polymer sheet 32.

The alert indicator 16 includes a predetermined alert message 18 that is substantially concealed until the light emitting polymer sheet 32 is illuminated. As shown in FIGS. 1 and 2, the predetermined alert message is simply "DUE," to indicate that the critical date has been reached. It should be apparent that many variations on the content of this message are possible depending on the particular use of the reminder device and the present invention is not intended to be limited to any particular use or message. The alert indicator 16 may include an audible signal generator (not shown) such as a piezoelectric buzzer that would produce an audible warning signal in addition to or instead of the visually perceptible signal.

The battery 28 is a three volt lithium battery formed as a flexible laminate having layers of anode and cathode materials separated by sheets of electrolyte. Commercially available batteries of this type having thicknesses on the order of 0.50 millimeters or less are suitable for the present invention. Such batteries are available through Battery Engineering. It will be understood by those skilled in the art that other types of batteries may be used without departing from the scope and spirit of the invention. For example, thin button-type batteries may be used. Also, all-plastic batteries such as those developed by researchers at Johns Hopkins University may be suitable. As shown in FIG. 4, the battery 28 is electrically interconnected to the real time clock 13 and the alert indicator 16 by the electrical connector trace arrangement 24.

The electronic reminder device 10 includes a cover layer 20 having a printing surface 21 upon which information indicia 22 may be printed. This information indicia 22 may include pre-printed material that is present when the device is supplied to the user. It may also include material printed on the surface by the user. Typically, the information supplied by information indicia 22 would be related to the particular use of the reminder device. For example, a card including the reminder device 10 that is intended to be a reminder of an appointment may include pre-printed business identification information along with a handwritten printed reminder of the time and date of the appointment.

The latter information would be written on the printing surface 20 of the reminder device 10 at the time the appointment is made. The cover layer 20 may be pre-applied to the reminder device 10 or provided separately for adhesive application by the user. Alternatively, the printing surface 20 may be printed directly to a visible portion of the substrate 11 or the battery 28.

The real time clock 13 of the electronic reminder device 10 is programmed using a user friendly software routine installed in a personal computer. It will be understood by those skilled in the art that less complex programming devices may also be used. Any device capable of generating clock and alarm setup data using the communication protocol of the real time clock 13 may be used. Clock and alarm data are downloaded from the computer and entered into the real time clock circuit 12 through the programming interface 14. For the Epson RTC 8593 real time clock, this is accomplished using an industry standard 12C communication protocol. Other real time clocks use a one-wire protocol or serial protocols. At the time of programming, the current date and time are entered along with a critical date and time of interest that may be up to a year from the date of programming. Periods of longer than one year are also possible depending on the real time clock chip used. Human readable verbiage will also typically be applied to the printing surface 21 at the time of programming to provide a visual reference to the user.

Operation of the real time clock 13 is initiated at the time of programming. When the critical date and time have been reached, the alarm function of the real time clock 13 causes the light-emitting polymer sheet 32 to be energized thus illuminating the predetermined alert message 18.

Measured though the printing surface 21, the reminder device 10 has a thickness on the order of one-half to two millimeters, depending on the components used. The maximum thickness of the reminder device 10 is measured through the real time clock 13. Depending on the device used for the real time clock 13, this maximum thickness may vary from approximately one-half millimeter to approximately five millimeters. The combination of flexibility and a thin profile allows the printing of the information indicia 22 directly to the printing surface 21 of the reminder device 10 using a conventional printer or typewriter. Alternatively, the information indicia 22 may be printed to the cover layer 20 before the cover layer is attached to the reminder device 10.

Figure 5:
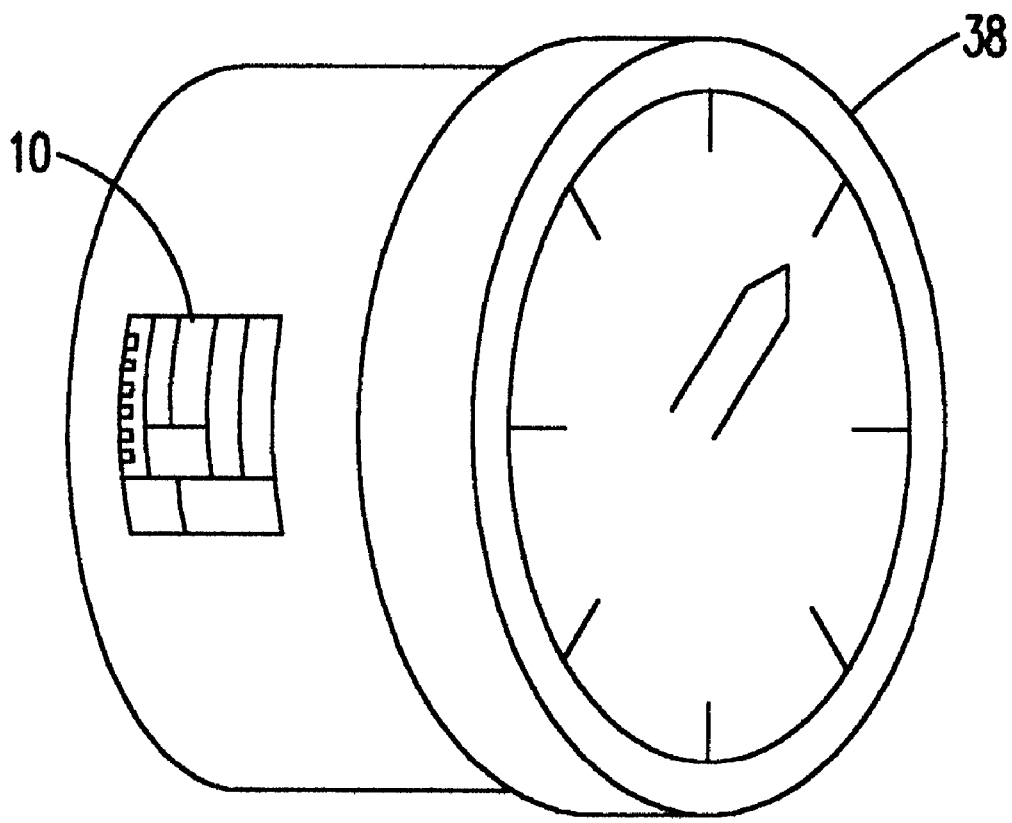
FIG. 5 is a perspective view of a programmable electronic label according to the preferred embodiment of the present invention wherein the electronic label has been applied to an instrument.

In one embodiment of reminder device 10, an adhesive layer 36 may be added to create a programmable electronic label. The electronic label according to the present invention is sufficiently thin and flexible to permit application to significantly contoured surfaces such as the curved casing of the instrument 38 illustrated in FIG. 5. The low profile of the reminder device 10 minimizes the potential for damage to the reminder device 10 or interference by the reminder device 10 with operation of instruments or machinery to which it is applied. This is of particular value when the purpose of the reminder device 10 is to signal when an instrument or machine is due for inspection or recalibration.

Figure 7:
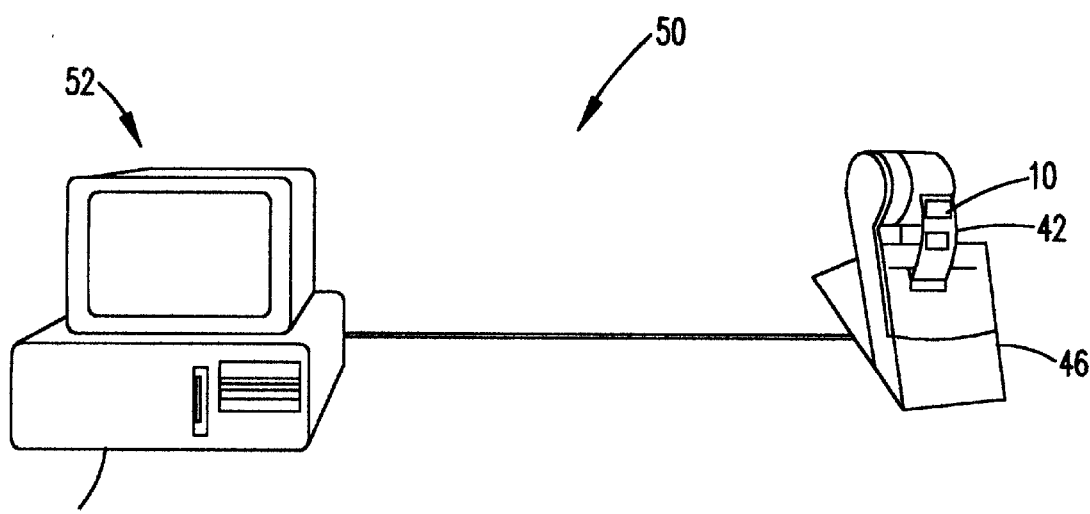
FIG. 7 is a schematic representation of a system according to the present invention for programming programmable electronic labels.

There are many instances where a large number of labels are needed by a single user. Accordingly, as shown in FIG. 7, the present invention includes a label programming system 50 for providing a large number of programmed electronic labels. The label programming system 50 uses a programming arrangement 52 that includes a personal computer 54 operatively attached to a printer 46 capable of receiving a continuous feed of reminder devices 10 having an adhesive backing 36.

Figure 6:
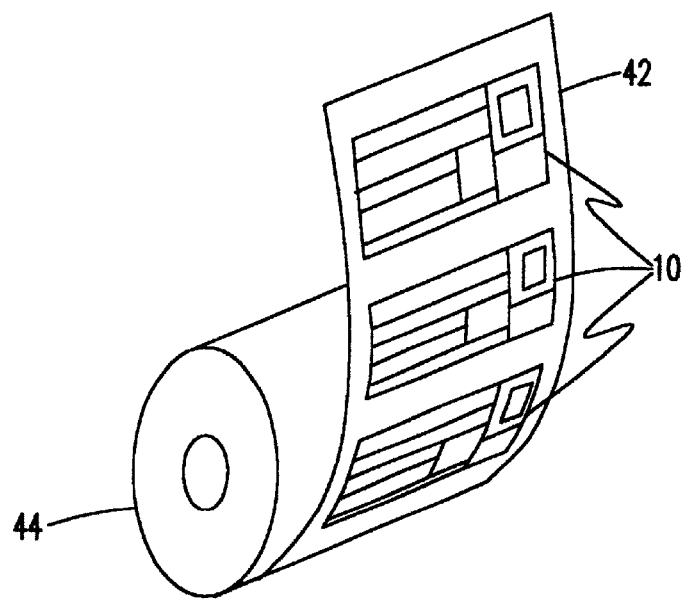
FIG. 6 is a perspective view of a plurality of programmable electronic labels arranged on a printing and dispensing roll.

The label programming system 50 for providing programmed electronic labels includes a plurality of reminder devices 10 removably applied to an elongate backing sheet 42. The backing sheet 42 is configured so that when a reminder device 10 is removed from the backing sheet 42, the adhesive layer remains with the reminder device 10 to permit the it to be adhesively applied to the desired surface. The reminder devices 10 are sufficiently thin and pliable that the backing sheet 42 with the reminder devices 10 applied may be wound into a printing/dispensing roll 44 as shown in FIG. 6. The printing/dispensing roll 44 of reminder devices 10 may be fed into a printer 46 which acts as both a visual indicia printer and a programming interface connector through which the reminder devices 10 may be programmed. When a reminder device 10 is fed to the printer 46, a mechanical contact (not shown) within the printer is connected to the programming interface 14 of the electronic label 40. If the programming interface 14 includes an infrared or electromagnetic interface arrangement instead of the electrical conductor pads 26, the mechanical contact would not be necessary. Programming instructions are downloaded from the computer 54 to the real time clock circuit 12 of the reminder device 10 via the computer's RS232C COM port and the printer 46. Substantially simultaneously, the printer 46 is commanded by the computer 54 to print human readable indicia to the printing surface 21 of the reminder device 10. In this way, a large number of reminder devices 10 may be rapidly and efficiently programmed with assurance that the human readable indicia corresponds to the programmed critical date and time. The reminder devices 10 may then be individually removed from the adhesive backing sheet 42 as needed.

It will be appreciated by those skilled in the art that many variations of the label programming system 50 are possible without departing from the spirit and scope of the present invention. For example, the programming connector through which the computer 54 is operatively connected to the programming interface 14 of a reminder device 10 need not be an integral part of the printer 46. Furthermore, the visual printing of human readable information on the printing surface 21 of the reminder device 10 need not be substantially simultaneous with the programming of the real time clock 13 in order to be within the spirit of the present invention. The printer 46 may, in fact, be manually operated rather than interconnected with the computer 54.

The present invention is highly advantageous compared to previous reminder methods and devices due to its simplicity, size and reliability. The inclusion of a real time clock permits the reminder device of the present invention to be operated based on absolute time and date rather than time intervals, more accurate making the device easier to program and use. Additionally, the risk of a programmer miscalculating a time interval is eliminated. Further, the crystal-controlled real time clocks used in the present invention present significant advantages in accuracy and longevity over previously used technology.

It will therefore be readily understood by those persons skilled in the art that the present invention is susceptible of a broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A programmable electronic indicia carrying device for providing a signal at a selectively predetermined date and time, said indicia carrying device comprising;

a pliant substrate comprising a flexible sheet;

a real time clock circuit mounted directly on said pliant substrate in a first area apart from a second area for printed indicia, said real time clock circuit being selectively programmable to provide an alarm signal substantially coincident with the predetermined date and time, said real time clock powered by a sheet-like, generally pliant battery;

an annunciator comprising a generally pliant light emitting polymer sheet operatively connected to said real time clock circuit, said annunciator providing a perceptible indication in response to said alarm signal; and a programming interface operatively connected to said real time clock circuit whereby the predetermined date and time may be programmed into said real time clock circuit, said pliant substrate, said pliant battery, and said pliant light emitting polymer sheet being laminated together to form a single sheet having a top surface for printed indicia in said second area, wherein said second area has a thinner cross-section than said first area having said real time clock to facilitate printing of said printed indicia.

2. A programmable electronic indicia carrying device according to claim 1 wherein said annunciator includes a visual indicator configured to provide a visually perceptible indication in response to said alarm signal indicating that the predetermined date and time has occurred.

3. A programmable electronic indicia carrying device according to claim 2 wherein said visual indicator includes a predetermined message that is revealed in response to said alarm signal.

4. A programmable electronic indicia carrying device according to claim 1 wherein said real time clock circuit includes an integrated circuit microprocessor.

5. A programmable electronic indicia carrying device according to claim 1 wherein said annunciator includes an audio generator that provides an audible alarm in response to said alarm signal.

6. A programmable electronic indicia carrying device according to claim 1 wherein said programming interface is selectively connectable to a computer for input of date and time data to program said real time clock circuit to emit said alarm signal at the predetermined date and time.

7. A programmable electronic label for providing a signal at a selectively predetermined expiration date and time, said label comprising:

a pliant substrate comprising a flexible sheet;

a real time clock circuit mounted directly on said pliant substrate in a first area apart from a second area for printed indicia, said real time clock circuit being selectively programmable to provide an alarm signal substantially coincident with the predetermined expiration date and time, said real time clock powered by a sheet-like, generally pliant battery;

an annunciator comprising a generally pliant light emitting polymer sheet operatively connected to said real time clock circuit, said annunciator providing a perceptible indication in response to said alarm signal;

a programming interface operatively connected to said real time clock circuit whereby the predetermined expiration date and time may be programmed into said real time clock circuit; and means for attaching said programmable electronic label to a surface associated with the predetermined expiration date and time, said pliant substrate, said pliant battery, and said pliant light emitting polymer sheet being laminated together to form a single sheet having a top surface for printed indicia in said second area, wherein said second area has a thinner cross-section than said first area having said real time clock to facilitate printing of said printed indicia.

8. A programmable electronic label according to claim 7 wherein said annunciator includes a visual indicator configured to provide a visually perceptible indication in response to said alarm signal indicating that the predetermined expiration date and time has occurred.

9. A programmable electronic label according to claim 8 wherein said visual indicator includes a predetermined message that is selectively revealed in response to said alarm signal.

10. A programmable electronic label according to claim 7 wherein said real time clock circuit includes an integrated circuit microprocessor.

11. A programmable electronic label according to claim 7 wherein said annunciator includes an audio generator that provides an audible alarm in response to said alarm signal.

12. A programmable electronic label according to claim 7 wherein said label includes a surface for carrying visually perceptible indicia.

13. A programmable electronic label according to claim 7 wherein said programming interface is selectively connectable to a computer for input of expiration date and time data to program said real time clock circuit to emit said alarm signal at the predetermined expiration date and time.

14. An electronic labeling system for providing electronic, selectively individually preprogrammed labels that each provide a signal at a selectively predetermined expiration date and time, said electronic labeling system comprising:

a plurality of programmable electronic labels, each label including a pliant substrate comprising a flexible sheet, a real time clock circuit mounted directly on said pliant substrate in a first area apart from a second area for printed indicia, said real time clock circuit being selectively programmable to provide an alarm signal substantially coincident with the predetermined expiration date and time, said real time clock powered by a sheet-like, generally pliant battery, an annunciator comprising a generally pliant light emitting polymer sheet operatively connected to said real time clock circuit, said annunciator providing a perceptible indication in response to said alarm signal, a programming interface operatively connected to said real time clock circuit whereby the predetermined expiration date and time may be programmed into said real time clock circuit;

means for attaching each said programmable electronic label to a surface associated with said predetermined expiration date and time, wherein each said programmable electronic label includes a surface for carrying visually perceptible indicia; and a communication interface connectable to said programming interface of each said electronic programmable label, said pliant substrate, said pliant battery, and said pliant light emitting polymer sheet being laminated together to form a single sheet having a top surface for printed indicia in said second area, wherein said second area has a thinner cross-section than said first area having said real time clock to facilitate printing of said printed indicia.

15. An electronic labeling system according to claim 14 and further comprising means for programming said real time clock circuit to emit said alarm signal at the predetermined time and date.

16. An electronic labeling system according to claim 14 wherein said annunciator includes a visual indicator configured to provide a visually perceptible indication in response to said alarm signal indicating that the predetermined expiration date and time has occurred.

17. An electronic labeling system according to claim 14 wherein said visual indicator includes a predetermined message that is selectively revealed in response to said alarm signal.

18. An electronic labeling system according to claim 14 wherein said real time clock circuit includes and integrated circuit microprocessor.

19. An electronic labeling system according to claim 14 further including a printer for printing visually perceptible indicia on each said programmable electronic label.

20. An electronic labeling system according to claim 19 wherein said printer is operatively interconnected with said communication interface and said means for programming so that said visually perceptible indicia may be printed on each said programmable electronic label substantially simultaneously with the programming of each said programmable electronic label by said means for programming.

21. An electronic labeling system according to claim 19 wherein said plurality of electronic programmable labels are removably attached to an elongate backing sheet and said printer is capable of accepting a continuous feed of said backing sheet for individual printing of each said electronic programmable label.

22. An electronic labeling system according to claim 15 wherein said means for programming includes a personal computer.

23. A flexible label providing an alarm indicating an expiration time, comprising:

a first layer comprising a flexible sheet, said first layer comprising;

a real time clock;

an alarm indicator formed from a pliant sheet operatively connected to said real time clock circuit; and a programming interface connected to said real time clock;

a second layer comprising a sheet-like pliant battery, said second layer affixed on said first layer leaving said alarm indicator exposed; and a third layer comprising a human readable label printed thereon, wherein a cross section of said flexible label is thinner at said third layer than a cross-section at said real time clock to facilitate printing;

wherein said real time clock is programmed via said programming interface to activate said alarm indicator when an expiration time has occured.

24. A flexible label providing an alarm indicating an expiration time as recited in claim 23 wherein said human readable label may be printed at a same time as said real time clock is programmed.

25. A flexible label providing an alarm indicating an expiration time as recited in claim 23 wherein said programming interface comprises a wireless data link.

26. A flexible label providing an alarm indicating an expiration time as recited in claim 23 wherein said programming interface comprises a laminated antenna.

27. A flexible label providing an alarm indicating an expiration time as recited in claim 23 wherein said programming interface comprises a infrared data link.

28. A flexible label providing an alarm indicating an expiration time as recited in claim 23 wherein said alarm indicator comprises a light emitting polymer film.

29. A flexible label providing an alarm indicating an expiration time as recited in claim 23 wherein said alarm indicator comprises a sound emitting piezoelectric film.

\* \* \* \* \*

UNITED STATES PATENT AND TRADEMARK OFFICE
CERTIFICATE OF CORRECTION

| | | |
|---|---|---|
| PATENT NO. | : 6,337,836 B1 | Page 1 of 1 |
| APPLICATION NO. | : 09/323460 | |
| DATED | : January 8, 2002 | |
| INVENTOR(S) | : Arthur F. Eidelson | |

It is certified that error appears in the above-identified patent and that said Letters Patent is hereby corrected as shown below:

Claim 1, Column 9, Line 20 - Delete "real time clock" to "real time clock circuit"
Claim 1, Column 9, Line 36 - Delete "real time clock" to "real time clock circuit"
Claim 7, Column 10, Line 1 - Delete "real time clock" to "real time clock circuit"
Claim 7, Column 10, Line 19 - Delete "real time clock" to "real time clock circuit"
Claim 14, Column 10, Line 56 - Delete "real time clock" to "real time clock circuit"
Claim 14, Column 11, Line 12 - Delete "real time clock" to "real time clock circuit"
Claim 23, Column 12, Line 8 - Delete "real time clock" to "real time clock circuit"
Claim 23, Column 12, Line 11 - Delete "real time clock" to "real time clock circuit"
Claim 23, Column 12, Line 19 - Delete "real time clock" to "real time clock circuit"
Claim 23, Column 12, Line 20 - Delete "real time clock" to "real time clock circuit"
Claim 24, Column 12, Line 25-26 - Delete "real time clock" to "real time clock circuit"

Signed and Sealed this
Fifth Day of April, 2011

David J. Kappos
*Director of the United States Patent and Trademark Office*